(12) United States Patent
Billig et al.

(10) Patent No.: US 7,404,834 B2
(45) Date of Patent: Jul. 29, 2008

(54) ETHYLENE OXIDE PLANT OPERATION

(75) Inventors: Barry Billig, Irvington, NY (US); James Mann, Brooklyn, NY (US)

(73) Assignee: SD Lizenzverwertungsgesellschaft mbH & Co. KG Lenbachplatz 6, Munich (DE)

( * ) Notice: Subject to any disclaimer, the term of this patent is extended or adjusted under 35 U.S.C. 154(b) by 618 days.

(21) Appl. No.: 11/056,222

(22) Filed: Feb. 11, 2005

(65) Prior Publication Data

US 2006/0183927 A1 Aug. 17, 2006

(51) Int. Cl.
*B01D 59/50* (2006.01)
*C07D 301/32* (2006.01)

(52) U.S. Cl. .......................... 55/321; 549/538

(58) Field of Classification Search ................. 549/538; 55/321

See application file for complete search history.

(56) References Cited

U.S. PATENT DOCUMENTS

| | | | | |
|---|---|---|---|---|
| 2,771,473 A | * | 11/1956 | Courter | 549/541 |
| 3,964,980 A | * | 6/1976 | Ozero | 203/42 |
| 5,646,087 A | | 7/1997 | Rizkalla et al. | 502/347 |
| 5,945,551 A | | 8/1999 | Rizkalla et al. | 549/534 |
| 6,184,175 B1 | | 2/2001 | Rizkalla | 502/347 |
| 6,533,843 B2 | | 3/2003 | Billig et al. | 95/172 |

* cited by examiner

*Primary Examiner*—Bernard Dentz
(74) *Attorney, Agent, or Firm*—Scully, Scott, Murphy & Presser, P.C.

(57) ABSTRACT

In an ethylene oxide process, the stripping and reabsorption operations, normally carried out in separate vessels, are carried out in a single vessel which is divided by a baffle into separate sections where reabsorption and stripping are carried out.

20 Claims, 2 Drawing Sheets

ETHYLENE OXIDE PLANT OPERATION

BACKGROUND OF THE INVENTION

1. Field of the Invention

The present invention relates to an apparatus useful for the formation of ethylene oxide, or more particularly for ethylene oxide reabsorption and carbon dioxide stripping on a commercial scale. This apparatus finds particular use as an improved single column ethylene oxide reabsorber/stripper vessel. According to this invention, the steps of ethylene oxide re-absorption and carbon dioxide stripping, which normally are carried out in separate vessels, are carried out in a single column vessel having an internal dividing baffle. The apparatus may also be used for other chemical processing systems that require reabsorption and stripping.

2. Description of the Related Art

The oxidation of ethylene to form ethylene oxide and the various recovery procedures associated therewith as well as additional conversion of ethylene oxide to ethylene glycol are well known and widely practiced commercially. See, for example, U.S. Pat. Nos. 5,945,551, 6,184,175, 5,646,087, and 6,533,843.

Typically, an ethylene oxide product is absorbed from the oxidation reaction gases in an aqueous absorbent liquid to form a dilute ethylene oxide solution. The ethylene oxide is stripped from the dilute aqueous solution and, the stripper overhead is sent to a condenser where the bulk of the water is condensed and separated. The ethylene oxide vapor stream from the stripper overhead concentrated in ethylene oxide is passed to a re-absorber where ethylene oxide is re-absorbed in water and thus separated from inerts which are vented. The ethylene oxide re-absorber solution, which also contains substantial amounts of dissolved carbon dioxide, is sent to a glycol feed stripper where carbon dioxide is separated by steam/inert gas stripping. Such conventional operation is illustrated in the attached FIG. 1.

The invention provides an improved apparatus wherein the functions of both a conventional re-absorber column and glycol feed stripper column are combined and carried out in a single column, which is divided by an internal baffle into separate reabsorption and stripping sections.

Such a combined single-column vessel offers several economic advantages, including simplification of industrial operations, and reduction in required floor area necessary for such equipment. Furthermore, since exposure of ethylene oxide to external fire is a significant safety hazard, a reduction in equipment would lessen the surface area of equipment requiring fireproofing, reduce potential exposure to fire, and improve the overall safety of the plant.

SUMMARY OF THE INVENTION

The invention provides a vessel for use in conjunction with an ethylene oxide recovery/stripping system which vessel comprises an outer wall defining a closed single column, an internal dividing baffle dividing the column into a reabsorption section and a separate stripping section, an inlet for introducing a vapor stream comprising ethylene oxide into the reabsorption section and for reabsorbing the ethylene oxide in an absorbent, a line for introducing the reabsorbed ethylene oxide into the stripping section, and a stripper for stripping contained carbon dioxide from the reabsorbed ethylene oxide.

The invention further provides an ethylene oxide recovery/stripping system which comprises: a vessel comprising an outer wall defining a closed single column, an internal dividing baffle for dividing the column into a reabsorption section and a separate stripping section, means for introducing a vapor stream comprising ethylene oxide into the reabsorption section and for reabsorbing the ethylene oxide in aqueous absorbent, means for introducing the reabsorbed ethylene oxide in aqueous absorbent into the stripping section, and means for stripping contained carbon dioxide from the reabsorbed ethylene oxide.

The invention still further provides a method of recovering ethylene oxide from aqueous ethylene oxide absorber liquid, comprising the steps of:

i) providing a vessel which comprises an outer wall defining a single column, an internal dividing baffle for dividing the column into a reabsorption section and a separate stripping section, an inlet for introducing a vapor stream comprising ethylene oxide into the reabsorption section and for reabsorbing the ethylene oxide in aqueous absorbent, a line for introducing the reabsorbed ethylene oxide in aqueous absorbent into the stripping section, and a stripper for stripping contained carbon dioxide from the reabsorbed ethylene oxide;

ii) introducing a vapor stream comprising ethylene oxide into the reabsorption section;

iii) passing the vapor stream over a lower packing bed within the reabsorption section;

iv) contacting the vapor stream with a cooled circulation solution such that a portion of ethylene oxide is absorbed into the circulation solution;

v) passing unabsorbed ethylene oxide and any inerts through at least one upper packing bed of the reabsorption such that the remainder of the ethylene oxide is absorbed in aqueous absorbent and removed from the inerts;

vi) removing inerts from the vessel;

vii) transporting reabsorbed ethylene oxide in aqueous absorbent to the top of the stripping section;

viii) stripping the reabsorbed ethylene oxide of carbon dioxide; and ix) passing the stripped ethylene oxide out of the vessel.

The invention also provides a vessel which comprises an outer wall defining a closed single column, a baffle within the outer wall dividing the column into a reabsorption section and a separate stripping section; at least one absorbent packing bed in the reabsorption section, and at least one stripping packing bed in the stripping section; an inlet for introducing a fluid stream into the reabsorption section and through the absorbent packing bed to produce an absorbed fluid, a line for introducing the absorbed fluid into the stripping section and through the stripping packing bed to produced a stripped fluid, and an outlet for discharging the stripped fluid from the stripping section.

DETAILED DESCRIPTION OF THE INVENTION

This invention combines the functions of an ethylene oxide re-absorber column and glycol feed stripper column such that their processes are carried out by a single column vessel. An internal divider baffle separates the single column into a reabsorption section and a stripping section.

Figure 1:
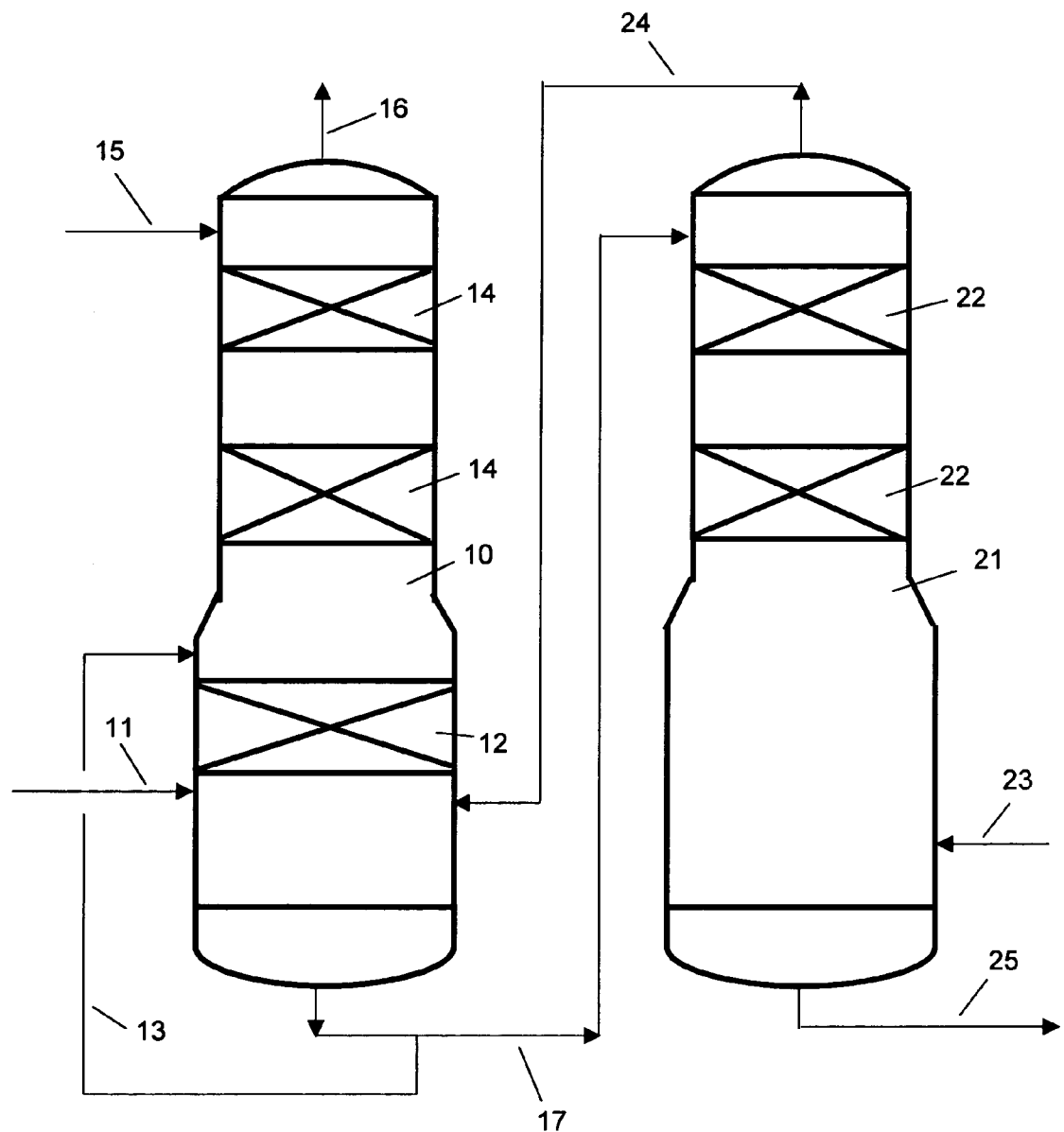
FIG. 1 shows a schematic representation of a prior art multi-column ethylene oxide reabsorbing and carbon dioxide stripping apparatus.

FIG. 1 shows a typical prior art apparatus arrangement for the operation of a conventional plant for ethylene oxide production. An inlet vapor stream comprising ethylene oxide from a stripping column condenser containing 80-90 vol % ethylene oxide and the balance water and inerts enters re-absorber column 10 via inlet vapor stream line 11. The inlet vapor stream flows through a lower packing bed 12, where a circulating solution of a cooled bottoms stream 13 quenches the inlet vapor stream, condensing 90-96% of the ethylene oxide. Uncondensed gas from the packing bed 12 flows through two upper packed beds 14, wherein the uncondensed gas is contacted with a water feed stream introduced via water feed stream line 15 which removes the balance of the ethylene oxide. An overhead stream is separated via overhead stream line 16 and is sent to a reclaim compressor for recycle of the contained ethylene back to the ethylene oxide reaction system. The water feed stream is adjusted in quantity to maintain the required ethylene oxide concentration for the feed to a glycol section of the plant, which typically ranges from about 3.8 to about 4.6 vol % ethylene oxide. A bottoms stream removed via bottoms stream line 17 contains some dissolved carbon dioxide which was contained in the inlet vapor stream line 11, and this carbon dioxide in the bottoms stream must be removed to prevent corrosion in a carbon steel glycol plant. Such is done in glycol feed stripper column 21.

The liquid bottoms stream from the re-absorber column 10 is sent to the top of glycol feed stripper column 21 via the bottoms stream line 17 and is passed over two packed beds 22, where the liquid bottoms stream is contacted with a stripping media such as steam and/or methane introduced via stripping media line 23. The stripping media strips out carbon dioxide and ethylene oxide, and the resulting vapor is sent via overhead recycle line 24 to column reabsorber 10 where the carbon dioxide is removed overhead and the ethylene oxide recovered. The bottoms of glycol feed stripper column 21 removed via bottoms removal line 25 is then suitable for use in the glycol plant or as feed to an ethylene oxide purification system.

Figure 2:
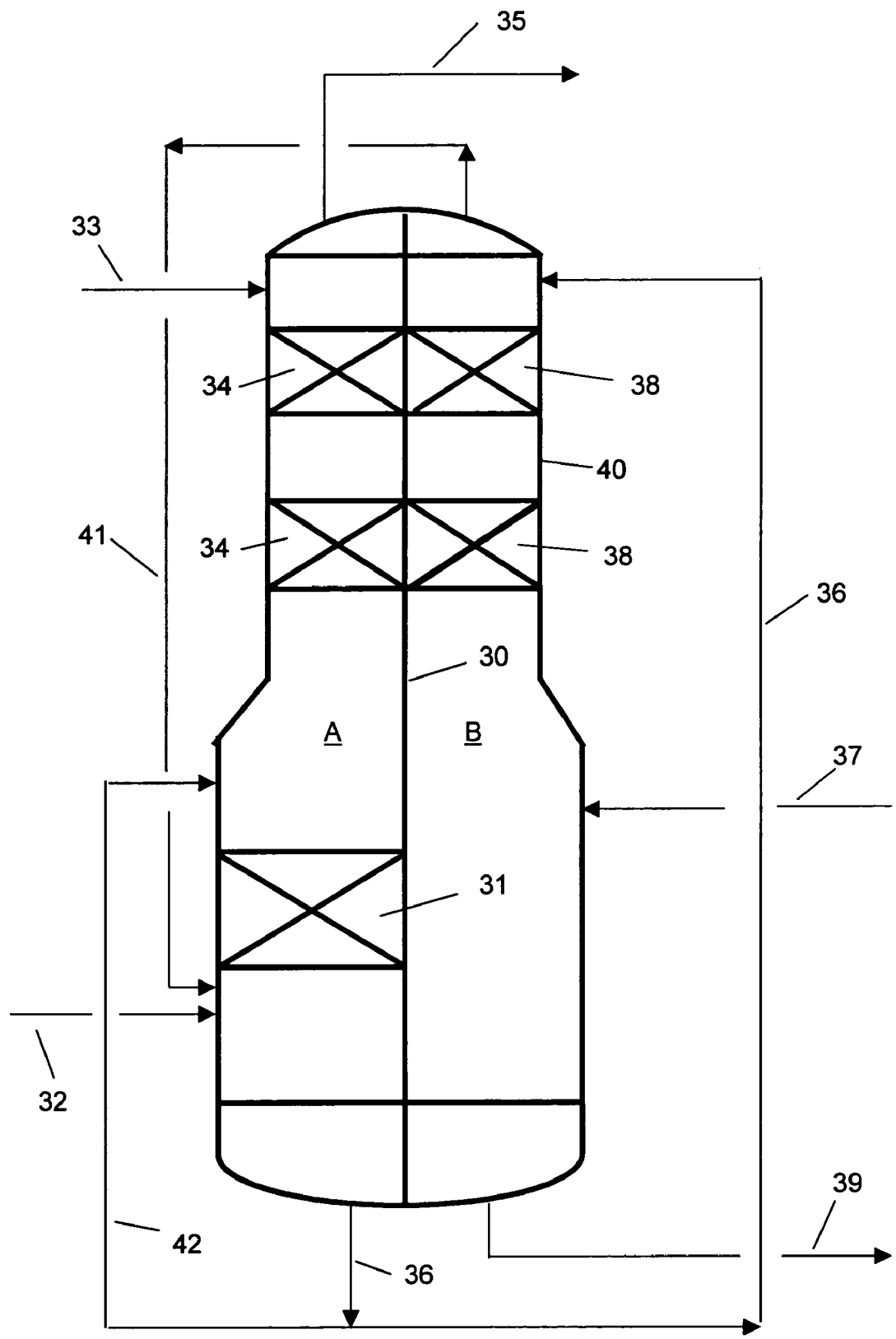
FIG. 2 shows a schematic representation of a single column reabsorber/stripper vessel according to the present invention.

The size of the upper sections of columns 10 and 21 in the conventional operation of FIG. 1 are essentially similar. Thus, it is possible to combine the functions of the top sections of these columns into a single column vessel 40 as illustrated in FIG. 2, which is divided by a dividing baffle 30 into two sections, A and B. By expanding the bottom diameter of the vessel 40 to provide additional liquid surge volume, it is possible to install the large packing bed 31 required in section A.

According to the invention, as shown in FIG. 2, a vapor stream from an ethylene oxide stripping column condenser (not shown) enters section A of column 40 via vapor stream inlet 32, where it is combined with an outlet vapor from section B via outlet vapor line 41 and passed over a lower reabsorber side packing bed 31. This bed 31 preferably uses a conventional type vapor liquid contact packing which is well known in the art. The combined vapor is contacted with a cooled circulation solution of bottoms liquid, which enters section A via bottoms removal line 42. Preferably from about 90 to about 95% of the ethylene oxide is absorbed in the circulation solution, and the solution is typically cooled in a water cooled exchanger (not shown) to a level ranging from about 7 to about 15° C. below the bottoms temperature. The cooling and circulation rate is preferably adjusted to achieve the desired bottoms ethylene oxide concentration by controlling the water feed stream 33, at the top of section A of the column 40. Unabsorbed ethylene oxide with inerts from the lower reabsorber side packing bed 31 passes to at least one upper reabsorber side packing bed 34, where the remainder of the ethylene oxide is absorbed in water and removed from the inerts. In a preferred embodiment two upper reabsorber side packing beds are present. The upper packing beds 34 also preferably comprise a conventional type vapor liquid contact packing which is well known in the art. The inerts vapor passes via inerts vapor line 35 to a reclaim compressor or to incineration for recovery or disposal.

The bottoms from section A, after separation of recycle is pumped via bottoms outlet line 36 to the top of section B where the liquid is stripped by steam and/or inert stripping gas introduced via stripping gas line 37, or by the use of a reboiler at the bottoms of section B (not shown). Typically at least one upper stripper side packing bed 38 is used to provide contact between the liquid and vapor in section B. In a preferred embodiment, two upper stripper side packing beds are present. These packing beds 38 also preferably comprise conventional type vapor liquid contact packing which is well known in the art The liquid is stripped free of carbon dioxide and other inerts and is pumped out of the bottom of section B via output line 39, and may be transported to a glycol section of the plant or an EO purification system, or the like.

The single column vessel of this invention may comprise any suitable material known in the art such as stainless steel and the like. Preferred materials nonexclusively include 304 stainless steel.

An important feature of the invention is the presence of a dividing baffle 30 within the single column vessel, which dividing baffle 30 separates the column into two areas, reabsorption section A and stripping section B. Preferably the dividing baffle 30 extends vertically from the top to the bottom of column 40. However, other arrangements may be used. The dividing baffle may comprise a material which is the same or different from the material of the vessel and is of an appropriate thickness to ensure structural integrity. Suitable materials nonexclusively include stainless steel such as 304 stainless steel. In a preferred embodiment, the dividing baffle comprises a material which is substantially the same as that material of the vessel.

Since both sections A and B operate at essentially equal pressure of 0.2-0.5 bars abs with a differential pressure of 0.1-0.2 bars, and the dividing baffle 30 is of a reasonable thickness to support the pressure difference. The functionality of the system is unchanged.

While reference is made herein to inlets, outlets, and lines in general terms, it should be understood that the inlets, outlets, and lines are simply access points through which a gas or fluid may be either supplied to or discharged from the vessel. Each inlet, outlet, or line may vary in diameter size and each may be equipped with a nozzle. The vessel may further include additional inlets, outlets and/or lines as desired by one skilled in the art to maintain the integrity of the vessel and as required by particular reaction processes. The vessel may further be equipped with meters that measure the pressure and/or temperature conditions within areas of the vessel. For example, the vessel may be equipped with an inlet/outlet/line through which is attached a pressure gauge, and another through which is attached a temperature gauge. The vessel may also be equipped with sampling mounts as desired.

The vessel is also capable of being heated or cooled well enough to have a desired temperature, as well as at a desired pressure. It should be understood that the vessel may also include additional features not specifically mentioned herein as may be conventionally known by one skilled in the art, particularly features useful for disassembling and moving the vessel.

The single column vessel 40 of the invention offers the advantage over the configuration of FIG. 1 of simplifying the equipment, and reducing the surface area of equipment which requires fire protection. Since ethylene oxide is an extremely dangerous material and exposure to external fire is a significant safety hazard, reduction of the potential exposure to external fire improves the overall safety of the plant. In addition, the single column vessel 40 significantly reduces the floor area required to house such an apparatus, thus reducing costs.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A vessel for use in conjunction with an ethylene oxide recovery/stripping system which vessel comprises an outer wall defining a closed single column, an internal dividing baffle dividing the column into a reabsorption section and a separate stripping section, an inlet for introducing a vapor stream comprising ethylene oxide into the reabsorption section useful for reabsorbing the ethylene oxide in an absorbent, and a line for introducing the reabsorbed ethylene oxide into the stripping section, for stripping contained carbon dioxide from the reabsorbed ethylene oxide.

2. The vessel of claim 1 further comprising a reboiler attached to the bottom of the stripping section.

3. The vessel of claim 1 wherein the reabsorption section comprises a lower reabsorber section packing bed and at least one upper reabsorber section packing bed, and the stripping section comprises at least one packing bed.

4. The vessel of claim 3 wherein the outer wall, the dividing baffle, and the packing bed comprise stainless steel.

5. An ethylene oxide recovery/stripping system which comprises: a vessel comprising an outer wall defining a closed single column; an internal dividing baffle for dividing the column into a reabsorption section and a separate stripping section, means for introducing a vapor stream comprising ethylene oxide into the reabsorption section, the reabsorption section including means for reabsorbing the ethylene oxide in aqueous absorbent; means for introducing the reabsorbed ethylene oxide in aqueous absorbent into the stripping section, the stripping section including means for stripping contained carbon dioxide from the reabsorbed ethylene oxide.

6. The system of claim 5 wherein the pressure in the reabsorption ranges from about 0.2 to about 0.5 bars.

7. The system of claim 5 wherein the pressure in the stripping section ranges from about 0.2 to about 0.5 bars.

8. The system of claim 5 wherein the difference in pressure between the reabsorption and the stripping section ranges from about 0.1 to about 0.2 bars.

9. The system of claim 5 further comprising a reboiler attached to the bottom of the stripping section.

10. The system of claim 5 wherein the reabsorption section comprises a lower reabsorber section packing bed and at least one upper reabsorber section packing bed, and the stripping section comprises at least one packing bed.

11. The system of claim 10 wherein the outer wall, the dividing baffle, and the packing bed comprise stainless steel.

12. A process for recovering ethylene oxide from aqueous ethylene oxide absorber liquid, comprising the steps of: i) providing a vessel which comprises an outer wall defining a single column, an internal dividing baffle for dividing the column into a reabsorption section and a separate stripping section, an inlet for introducing a vapor stream comprising ethylene oxide into the reabsorption section, the reabsorption section including means for reabsorbing the ethylene oxide in an aqueous absorbent, a line for introducing the reabsorbed ethylene oxide in the aqueous absorbent into the stripping section, the stripping section including means for stripping contained carbon dioxide from the reabsorbed ethylene oxide; ii) introducing a vapor stream comprising ethylene oxide into the reabsorption section; iii) passing the vapor stream over a lower packing bed within the reabsorption section; iv) contacting the vapor stream with a cooled circulation solution such that a portion of ethylene oxide is absorbed into the circulation solution; v) passing unabsorbed ethylene oxide and any inerts through at least one upper packing bed of the reabsorption such that the remainder of the ethylene oxide is absorbed in aqueous absorbent and removed from the inerts; vi) removing inerts from the vessel; vii) transporting reabsorbed ethylene oxide in aqueous absorbent to the top of the stripping section; viii) stripping the reabsorbed ethylene oxide of carbon dioxide; and ix) passing the stripped ethylene oxide out of the vessel.

13. The process of claim 12 wherein step (vi) comprises passing the inerts to a reclaim compressor or to incineration for recovery or disposal.

14. The process of claim 12 wherein step (viii) comprises passing the liquid over at least one upper packing bed of the stripping section, and contacting the liquid with steam and/or inert stripping gas.

15. The process of claim 12 wherein the outer wall, the dividing baffle, and the packing bed comprise stainless steel.

16. The process of claim 15 wherein the pressure in the reabsorption section ranges from about 0.2 to about 0.5 bars.

17. The process of claim 15 wherein the pressure in the stripping section ranges from about 0.2 to about 0.5 bars.

18. The process of claim 15 wherein the difference in pressure between the reabsorption section and the stripping section ranges from about 0.1 to about 0.2 bars.

19. A vessel which comprises an outer wall defining a closed single column, a baffle within the outer wall dividing the column into a reabsorption section and a separate stripping section; at least one absorbent packing bed in the reabsorption section, and at least one stripping packing bed in the stripping section; an inlet for introducing a fluid stream into the reabsorption section and through the absorbent packing bed to produce an absorbed fluid, a line for introducing the absorbed fluid into the stripping section and through the stripping packing bed to produce stripped fluid, and an outlet for discharging the stripped fluid from the stripping section.

20. The vessel of claim 19 wherein the reabsorption section comprises a lower reabsorber section packing bed and at least one upper reabsorber section packing bed, and the stripping section comprises at least one packing bed.

* * * * *